United States Patent
Saab et al.

(10) Patent No.: US 11,457,914 B2
(45) Date of Patent: Oct. 4, 2022

(54) SYSTEM, APPARATUS, AND METHOD FOR WOUND CLOSURE

(71) Applicant: Ihab Saab, Detroit, MI (US)

(72) Inventors: Ihab Saab, Detroit, MI (US); Ayana Dambaeva, Cleveland Heights, OH (US); Megan Flint, Madison, WI (US); Sunny Karnan, Ann Arbor, MI (US); Monica Patel, Vernon Hills, IL (US); Matthew Pierce, Milford, MI (US)

(73) Assignee: ISaab Innovations LLC, Troy, MI (US)

( * ) Notice: Subject to any disclaimer, the term of this patent is extended or adjusted under 35 U.S.C. 154(b) by 414 days.

(21) Appl. No.: 16/387,663

(22) Filed: Apr. 18, 2019

(65) Prior Publication Data

US 2019/0321031 A1    Oct. 24, 2019

Related U.S. Application Data

(60) Provisional application No. 62/659,230, filed on Apr. 18, 2018.

(51) Int. Cl.
| | | |
|---|---|---|
| *A61B 17/04* | (2006.01) | |
| *A61B 17/08* | (2006.01) | |
| *A61B 17/068* | (2006.01) | |

(52) U.S. Cl.
CPC ...... *A61B 17/0491* (2013.01); *A61B 17/0466* (2013.01); *A61B 17/068* (2013.01); *A61B 17/08* (2013.01); *A61B 2017/0496* (2013.01)

(58) Field of Classification Search
CPC ............ A61B 17/0491; A61B 17/0466; A61B 17/0467; A61B 14/0469; A61B 17/0487; A61B 17/0493; A61B 17/068; A61B 17/0682; A61B 17/0684; A61B 17/0686; A61B 17/072; A61B 17/07207;
(Continued)

(56) References Cited

U.S. PATENT DOCUMENTS

| | | | | |
|---|---|---|---|---|
| 5,792,151 A | * | 8/1998 | Heck | ................ A61B 17/12009 112/169 |
| 7,048,748 B1 | | 5/2006 | Ustuner | |

(Continued)

OTHER PUBLICATIONS

Irrigate Definition & Meaning, Dictionary.com, https://www.dictionary.com/browse/irrigate, accessed Apr. 22, 2022. Copyright 2022 Dictionary.com LLC (Year: 2022).*

(Continued)

*Primary Examiner* — Kathleen S Holwerda
*Assistant Examiner* — Kankindi Rwego
(74) *Attorney, Agent, or Firm* — Brooks Kushman P.C.

(57) ABSTRACT

A medical wound closure device for portable and single usage is provided. The device has first and second approximation members supported by a housing, a wound closure mechanism supported for translation within the housing by a translational drive mechanism and configured to insert at least one fastener into tissue to close the wound, and a controller configured to operate the translational drive mechanism to move the wound closure mechanism relative to the housing, and operate the wound closure mechanism to insert the at least one fastener. Automatic suturing mechanisms are provided. A method of closing a wound using a device is also provided.

10 Claims, 7 Drawing Sheets

(58) Field of Classification Search
CPC ..... A61B 17/08; A61B 17/083; A61B 17/085; A61B 17/10; A61B 2017/0495; A61B 2017/0496; A61B 2017/0498; A61B 2017/0688; A61B 2017/081; A61B 2017/086; A61B 2017/088; A61B 34/20; A61B 34/30; A61B 34/32; A61B 34/35; A61B 34/37; A61B 34/70

USPC ................ 606/130, 144, 215, 216, 217, 218

See application file for complete search history.

(56) References Cited

U.S. PATENT DOCUMENTS

| | | | | |
|---|---|---|---|---|
| 2009/0012538 | A1* | 1/2009 | Saliman | A61B 17/0491 606/228 |
| 2015/0127024 | A1* | 5/2015 | Berry | A61B 17/0491 606/145 |
| 2016/0106516 | A1* | 4/2016 | Mesallum | A61B 90/50 606/130 |

OTHER PUBLICATIONS

Lambert et al., "Benchmarking and measuring the comparative efficiency of emergency medical services in major US cities", Benchmarking: An International Journal, vol. 16, Issue 4, 2009, pp. 543-561.

Frick et al., "Resistance forces acting on suture needles", Journal of Biomechanics, 34, 2001, pp. 1335-1340.

American National Standard, "Human factors engineering—Design of medical devices", 2010, 465 pages.

Nawar et al., "National Hospital Ambulatory Medical Care Survey: 2005 Emergency Depailment Summary", Advance Data, U.S. Department of Health and Human Services, No. 386, Jun. 29, 2007, 32 pages.

Mosby, "Wounds and Lacerations: Emergency Care and Closure", 2005, 309 pages.

Sobrino et al., "Timing and causes of death after injuries", Baylor University Medical Center Proceedings, vol. 26, No. 2, Apr. 2013, pp. 120-123.

Capek et al.,"The analysis of forces needed for the suturing of elliptical skin wounds", Med. Biol. Eng. Comput., vol. 50, 2012, pp. 193-198.

American National Standard, "Medical devices—Part 1: Application of usability engineering to medical devices", 2015, 52 pages.

American National Standard, "Sterilization of health care products—Ethylene oxide—Requirements for development, validation and routine control of a sterilization process for medical devices", 2015, 95 pages.

Journal of Emergency Medical Services, "Wilderness Wound Management", Oct. 14, 2008, 5 pages.

https://lacerationrepair.com/techniques/alternative-wound-closure/tissue-adhesive-tape, "Closing the Gap—Tissue Adhesive Tape", Jan. 2017, 6 pages.

Department of Defense Test Method Standard, "Environmental Engineering Considerations and Laboratory Tests", Oct. 31, 2008, 804 pages.

NHS, "How do I care for wound treated with skin glue?", Mar. 20, 2018, 3 pages.

Guidance for Industry and FDA Staff, "Medical Devices with Sharps Injury Prevention Features", U.S. Department of Health and Human Services, Aug. 9, 2005, 20 pages.

* cited by examiner

SYSTEM, APPARATUS, AND METHOD FOR WOUND CLOSURE

CROSS-REFERENCE TO RELATED APPLICATIONS

This application claims the benefit of U.S. provisional application Ser. No. 62/659,230 filed Apr. 18, 2018, the disclosure of which is hereby incorporated in its entirety by reference herein.

TECHNICAL FIELD

Various embodiments relate to a system and a method for wound closure.

BACKGROUND

Lacerations, deep cuts, or tears in the skin or flesh may require professional medical attention for closure. For a laceration caused by injury, a significant time may pass before reaching professional medical help depending on the location of the person. For example, over six million lacerations are treated annually in emergency medical departments in the United States. Common conventional protocol for treating a wound injury includes applying gauze and pressure, medical glue, or medical tape until appropriate professional medical attention is reached; however, this may lead to increased risk of infection and/or blood loss for the patient and may result in sepsis or shock. With the use of gauze and pressure, the wound may re-open due to stresses on the surrounding tissue or an inadequate closure, and additional bleeding may occur. Medical glue only secures the top layers of skin or tissue, can be applied only after active bleeding has stopped, and may be difficult to remove after application. Medical tape only secures the top layers of skin or tissue, can be applied only after active bleeding has stopped, and is relatively weak such that there is a risk of the wound re-opening based on stresses or excess blood or fluid.

SUMMARY

In an embodiment, a medical wound closure device for portable and single usage is provided. The device has a housing, and first and second approximation members supported by the housing. Each approximation member has a distal end region configured to move from a first position adjacent to the housing to a second position spaced apart from the housing to approximate a wound. A wound closure mechanism is supported for translation within the housing by a translational drive mechanism, and the wound closure mechanism is configured to insert at least one fastener into tissue to close the wound. A controller is configured to operate the translational drive mechanism to move the wound closure mechanism relative to the housing, and operate the wound closure mechanism to insert the at least one fastener.

In another embodiment, an automatic suturing mechanism is provided with a first electric motor supported by a main bracket, a claw bracket connected to a shaft of the first electric motor for rotation therewith, a second electric motor supported by the claw bracket, and first and second claw members rotatably connected to the claw bracket. Each claw member has a gripping surface. The first claw member is driven by a shaft of the second electric motor and is configured to move between a first position with the gripping surfaces of the first and second claw members in contact with one another and a second position with the gripping surfaces of the first and second claw members spaced apart from one another.

In yet another embodiment, an automatic suturing mechanism is provided with a support frame, an electric motor connected to the support frame and having a driveshaft, a series of pairs of rollers supported by the support frame for rotation relative to the support frame, and a gear mechanism drivingly connecting the driveshaft of the motor with at least one of the rollers in each pair of rollers. Each pair of rollers is spaced apart from adjacent pairs of rollers about the frame such that a suture needle may be passed from one pair of rollers to a subsequent adjacent pair of rollers along a path forming a continuous loop.

In another embodiment, a method of closing a wound using a device is provided. A housing of a device is positioned over a wound. First and second approximation members are extended away from the device housing thereby pulling tissue on either side of the wound towards the housing and towards the wound to approximate the wound. A wound closure mechanism and a translational drive mechanism of the device are controlled using a controller to close a wound by inserting at least one fastener along the wound.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
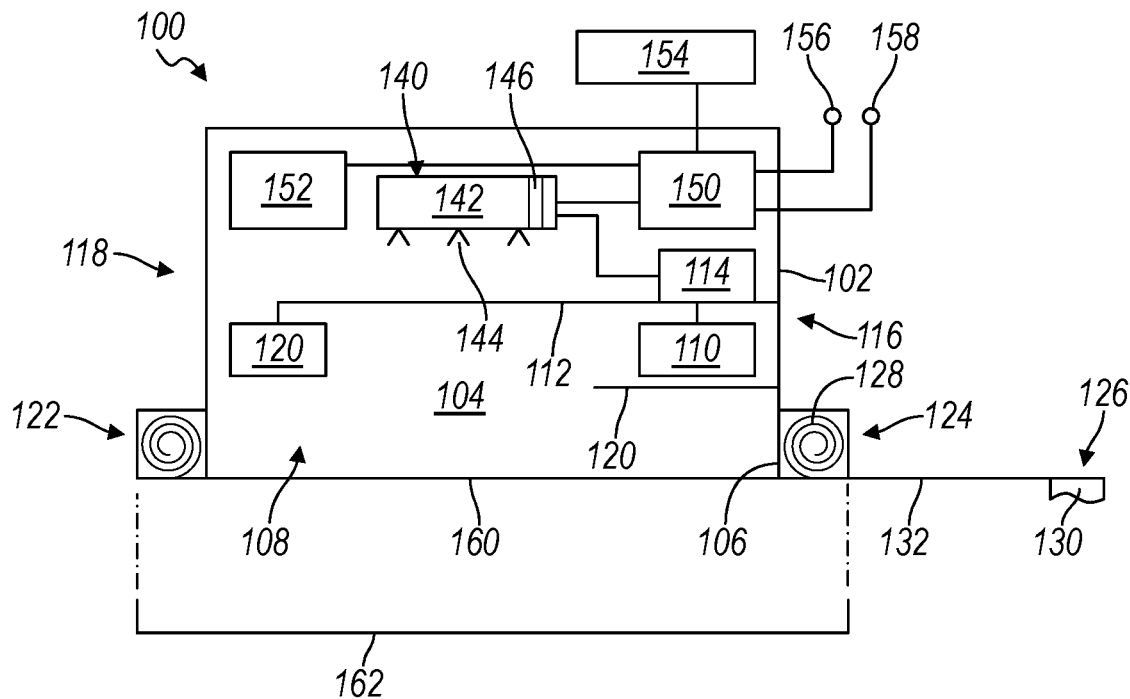
FIG. 1 illustrates a schematic view of a device for wound closure according to an embodiment.
Figure 2:
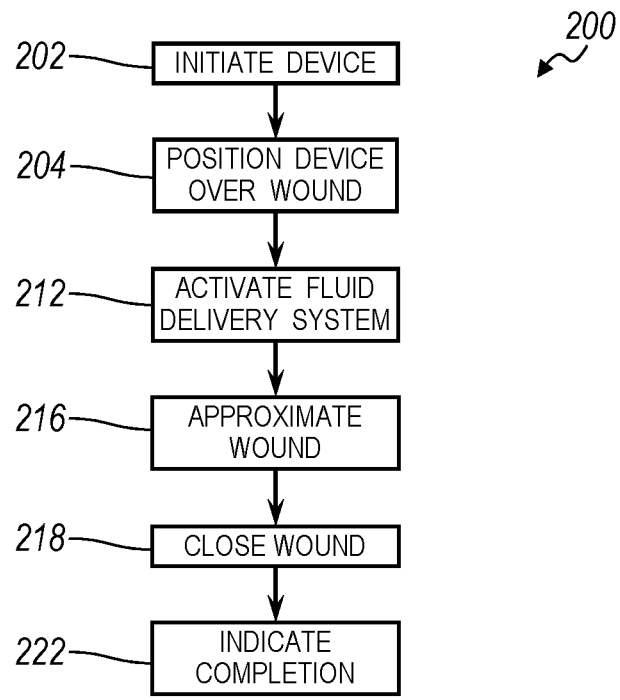
FIG. 2 illustrates a flow chart for a method of wound closure according to an embodiment.

FIG. 1 illustrates a schematic view of an apparatus or device 100 for wound closure according to an embodiment. The device 100 may be configured as a disposable device for one-time use, and provides an automated or semi-automated alternative to current laceration treatments. In various examples, the device 100 is configured for use by an individual without medical training, including self-administered use by the injured person or patient. In other examples, the device 100 is used by medical personnel without the certification or qualifications required to perform other wound closure methods, such as suturing. In further examples, the device 100 is used in a medical setting, for example by a medical doctor, as an automated wound closure device.

The device, system, and method according to the present disclosure may provide for wound closure when professional medical attention is unavailable. For example, the device 100 may be used when the injured person is remotely located from medical facilities or assistance, e.g. in a rural or other remote area, and when there may be a significant time delay before medical attention or facilities may be reached based on response time and/or transport time. Approximately twenty percent of the U.S. population resides in a rural area where response times may be longer. Emergency responders in these areas may be untrained or not have the required certification for some wound closure techniques, such as suturing. Alternatively, the injured person may be in a remote area, for example, backcountry or wilderness areas, and be difficult to access or extract. The device and method according to the present disclosure provides for wound closure by an individual, including by the patient, in situations where they are at increased risk for blood loss or infection due to lack of access to medical facilities.

The device 100 may be used as a temporary wound closure until the patient is able to reach professional medical care, where medical personnel may assess the injury and decide to further treat or re-close the laceration or wound.

In alternative examples, the device, system and method is used in a medical setting by trained medical professionals to provide an automated or semi-automated closure of tissue, or is used in a medical setting by medical personnel without the required certification for closure techniques such as suturing or stapling.

Generally, the device 100 is used for closure of lacerations or wounds that are not located near a major blood vessel, such as the jugular vein. The device may be used for closing lacerations in one or more dermal layers of the skin, and/or may be used for closing lacerations in other tissues.

The device 100 may be configured to clean the wound, numb or otherwise treat the injured area, bring the edges of the wound together, and close the wound. The device 100 incorporates a control system that automates or semi-automates the process, and may provide step-by-step instructions, alerts, or updates to the user.

The apparatus 100 has a housing 102 that defines an interior region 104 and has a lip 106 or edge region circumferentially surrounding an aperture 108. The housing 102 may be formed from a plastic material. The housing 102 may have various shapes, and a box-shape is illustrated as a non-limiting example. The lip 106 may be configured to contact the skin or tissue of the injured person and surround the wound or laceration.

The housing 102 may define a series of markings or other indicators to aid the user in positioning the device correctly with respect to the wound or laceration. For example, the housing 102 may be provided with lines, arrows, or other visual markings to aid in the positioning and alignment of the housing relative to the wound or laceration. The housing 102 may additionally have one or more transparent regions or windows that are provided with indicators or alignment markers to allow the user to correctly position and orient the device 100 with respect to the wound or laceration and view the wound or a portion of the wound when covered by the housing. In further examples, the housing 102 supports one or more sensors or devices that can detect the location and edges of a wound, and aids the user in positioning the device, for example by providing feedback or instructions from the human machine interface, e.g. a laser and photodetector system may be used as a guide to center the housing 102 over the wound. The housing 102 may also depict or illustrate an approximate wound size that may be closed using the device 100 on the outer surface of the housing to aid the user of the device in properly using the device. In further examples, the device 100 may incorporate a sensor to detect the existence of one or more major blood vessels immediately adjacent to the wound and in a region associated with the closure to prevent interference with the blood vessel, or to detect a blood flow for example, by sensing illumination of the vessels.

The device 100 may be provided in varying sizes. In one example, the housing 102 is relatively small to allow for ease of portability, and the overall dimensions of the device 100 are provided such that the device is between 2.5 and 7.5 cm in width, 5 and 13 cm in length, and 2.5 and 7.5 cm in height. The device 100 may have an overall weight ranging between 0.1 and 1 kilograms. In other examples, the device 100 and housing 102 may be smaller or larger based on the size of the wound that it is intended to close and/or the medical application.

For example, the device 100 may be sized and designed for closure of a wound or laceration that is approximately three centimeters in length, or for closure of a three-centimeter long section of a longer wound. The device 100 may be designed to provide a specified number or closures, such as three sutures or staples, within this distance. Of course, other sizes for the device 100 are contemplated, and this may be at least partially based on the number of closures delivered by the device and the size of the intended wound for closure. For wounds that are longer than the device 100 is sized for use with a system of multiple devices 100 may be positioned along the wound and work cooperatively to close the wound according to various embodiments and as described below. Additionally, as wounds may be non-linear, e.g. jagged, the wound or laceration may be discretized into sections, and multiple devices 100 may be used to close each section to close the entire wound.

In other examples, the device 100 closes a longer wound length. For example, with braided or monofilament suture material, barbed sutures, other forms of suture material, staples, clips, or other closure fasteners, the device size and number of fasteners may be increased to close a longer wound section. Alternatively, the suturing mechanism may include an addition feed mechanism by which the closure mechanism may pick up another suture needle and suture to continue the wound closure.

In further examples, the device 100 may be sized for continuous closure of a longer wound or laceration. For example, the device may be sized for use with a specific medical procedure, such as closing a midline abdominal laparotomy incision, a thoracotomy incision, a sternotomy incision, or any other long linear incision made during surgery.

The housing 102 supports a wound closure mechanism 110 positioned at least partially within the interior region 104. The wound closure mechanism 110 is described in further detail below according to various embodiments, and may include an automatic suturing mechanism or an automatic fastening mechanism employing staples or clips. The wound closure mechanism 110 is provided with braided or monofilament suture material, barbed sutures, other forms of suture material, staples, clips, or other closure fasteners to close the wound.

In one example, the wound closure mechanism 110 is supported within the housing 102 by a translational drive mechanism 112. The translational drive mechanism 112 may move the closure mechanism 110 along a linear path, or may move the closure mechanism 110 along a non-linear path according to other examples. The translational drive mechanism 112 may include a worm drive, a belt and track system, or the like. The translational drive mechanism 112 may also incorporate an actuator 114 such as an electric motor. In some embodiments, the actuator 114 is also used as an actuator for the closure mechanism 110. The wound closure mechanism 110 may be configured to slide or translate along the translational drive mechanism 112 from a first end region 116 of the housing to an opposite, second end region 118. In other embodiments, a portion of the wound closure mechanism 110 moves along the track of the drive mechanism 112, and sequentially engages with other translationally fixed portions of the wound closure mechanism 110, for example, a fastener mechanism may have a drive member moving along the track to sequentially implant and shape a series of fasteners such as staples or clips positioned in a cartridge. The cartridge may be fixed or may move along with the drive member.

Guard members 120 may be provided at the ends 116, 118 of the translational drive mechanism 112 such that the wound closure mechanism 110 is covered by the guard member 120 before operation of the device 100 or once it has reached the second end region 118 and has completed its wound closure operation. The guard member 120 may act as a sharps guard or the like until the device 100 may be safely disposed of, for example, by a medical waste facility.

The housing 102 also supports a pair of approximation members 122, 124. The approximation members 122, 124 are provided on opposite sides of the housing 102, and are used to pull the skin or tissue on either side of the wound towards one another, thereby bringing the wound edges together to approximate the wound, and also to provide wound edge eversion. The wound or laceration is approximated such that the wound edges are barely touching to decrease tension from the suture and to facilitate the suturing or other closure process. The wound may be approximated such that the distance between opposite edges of the wound is approximately one millimeter or less. For wound eversion, the edges of the wound are pointed upwardly and away from the wound. Wound eversion may decrease infection risk, scar tissue formation, and inflammation.

Each approximation member 122, 124 has a distal end 126 that is configured to move from a first position adjacent to the housing 102 as shown for member 122, to a second position that is spaced apart from the housing 102 as shown for member 124. Each approximation member 122, 124 may include a tensioning member 128 to draw the distal end 126 towards the housing 102 when in the second position to approximate the wound. The distal end 126 of the approximation member may be provided with an adhesive material 130 such as adhesive strip to temporarily attach the distal end 126 to the skin of the injured person. The tensioning member 128 may include a coil spring member, or another spring element. In further examples, the tensioning member may be provided by an elastic material.

The approximation members 122, 124 may include a sheet of material 132, such as a plastic film, that is rolled about a coil spring member 128. The user extends and unrolls the sheet 132, attaches the distal end 126 of the sheet to the skin via the adhesive material 130, and the coil spring member 128 then draws the skin towards the device housing 102. When both approximation members 122, 124 are attached to the skin, the wound edges are drawn together and approximated, and wound eversion may also be provided. In further examples, the sheet 132 of material may be formed from an elastic material to inherently provide tensioning without a separate tensioning member, or in addition to a tensioning member 128 such as a spring.

A fluid delivery system 140 may be positioned within the housing 102. The fluid delivery system 140 has one or more reservoirs 142 fluidly connected to one or more nozzles or ports 144. The reservoirs 142 may be pre-filled canisters containing a pressurized fluid, or the reservoirs 142 may incorporate a plunger 146 for fluid delivery as shown. The plunger 146 may be driven by an actuator, and in one embodiment is connected to the actuator 114 of the translational drive mechanism. In one example, operation of the actuator 114 is configured such that the plunger 146 is moved first for fluid delivery prior to the actuator 114 moving or operating the closure mechanism 110. For a pressurized canister as a reservoir 142, one or more valves may be controlled to initiate fluid delivery or a seal may be broken or punctured, for example, by a pin connected to the translation drive mechanism 112. The nozzles 144 are sized and positioned to direct a predetermined volume of fluid to the wound.

The device may be provided with a reservoir 142 of an irrigation fluid, such as a saline solution. For example, the reservoir may contain an ethyl chloride that is used to propel normal saline, e.g. 0.9% NaCl, a chlorhexidine-based solution, or any other cleaning solution, through the nozzles 144. The ethyl chloride solution may act as a local anesthetic that is sprayed in the wound by the nozzles 144.

The fluid delivery system 140 may additionally have a second reservoir similar to reservoir 142 that contains another fluid, such as a local anesthetic or numbing agent, a coagulation agent, an anti-septic agent, or the like.

In further examples, the reservoir 142 contains a single fluid that provides both irrigation and other functions, such as numbing, coagulation, anti-septic, or the like, and may be a mixture of more than one fluid.

In other examples, the device 100 may have more than two reservoirs 142, or may be provided without the fluid delivery system 140 such that a separate fluid system may be required for use to irrigate and/or numb the wound prior to using the device.

The housing 102 also supports a controller or control system 150. The control system 150 is in communication with various components of the device 100, including the wound closure mechanism 110, the linear drive mechanism 112, and the fluid delivery mechanism 140. The controller 150 operates to control the various actuators and motors of the various components. The device 100 and its components may have various sensors to provide inputs or feedback to the controller 150. The controller 150 receives power from a battery 152, which also powers various actuators and components in the device. The controller 150 is additionally in communication with a human machine interface 154.

It is recognized that any circuit or other electrical device disclosed herein may include any number of microprocessors, integrated circuits, memory devices (e.g., FLASH, random access memory (RAM), read only memory (ROM), electrically programmable read only memory (EPROM), electrically erasable programmable read only memory (EEPROM), or other suitable variants thereof) and software which co-act with one another to perform operation(s) disclosed herein. In addition, any one or more of the electrical devices as disclosed herein may be configured to execute a computer-program that is embodied in a non-transitory computer readable medium that is programmed to perform any number of the functions as disclosed herein.

In some examples, the controller 150 is provided with a receiver 156 and a transmitter 158. In one example, multiple devices 100 may be used in conjunction with one another, as described in further detail below. In this scenario, each device 100 may be in communication with other adjacent devices via signals exchanged between the devices via the receivers and transmitters 156, 158, and the controller 150 may operate the device 100 based on an input to another device, and based on the operating status of the other device(s).

The human machine interface 154 may include one or more display screens, a series of indicator lights, and/or a speaker to provide audible alerts or instructions. The human machine interface 154 may additionally include an "on" or start or input button, and additional buttons for user inputs. The display screen may provide visual indicators such as text or icons relating to the operating state of the device 100, and any warnings or errors. The indicator lights may additionally be provided to show status of the device 100, and may be provided by a series of lights and/or different colored lights, for example, by use of light emitting diodes. The speaker of the human machine interface 154 may provide audible step-by-step instructions for the user, for example via voice commands, or indicate a status or warning of the device via beeps, tones, or the like.

A film 160 or other member may be provided to cover the aperture 108 and maintain sterilization of the components within the interior region 104 of the housing 102 before use. The film 160 may be attached to the lip region 106 of the housing. Prior to use, the user removes the film 160 from the device 100 to expose the interior region.

The device 100 may additionally include a cover member 162. The cover member 162 may be formed from a plastic material. The cover member 162 is removed prior to use, and then replaced after use. In one example, the cover member 162 detaches and reattaches from the housing 102 in different manners. The cover member 162 is reattached to the housing 102 after use such that it cannot be easily removed and further provide a guard structure over the interior region 104 until the device 100 may be safely disposed of at a medical waste facility. For example, the cover 162 may slide off of the housing 102, and snap back onto the housing 102.

FIGS. 2-6 illustrate a method 200 of using a device, such as the device 100 as described above with respect to FIG. 1. In other embodiments, various steps in the method 200 may be combined, rearranged, or omitted.

At step 202, the device 100 is initiated, and any covers 162 or films 160 are removed from the device. The controller 150 may be configured to begin operating and provide step-by-step instructions to the user at any point during the method 200. The controller 150 is described as beginning operation at step 202; however, in other embodiments, the controller 150 may be activated at a later step. The user may use the human machine interface 154 to press an "on" button on the device 100 in conjunction with removing the film and cover, or in alternative examples the removal of the film 160 or cover 162 may operate a switch that automatically begins device 100 and controller 150 operation. The controller 150 and human machine interface 154 may be configured to provide an alarm if the user tries to remove the device 100 before the procedure is completed.

Figure 3:
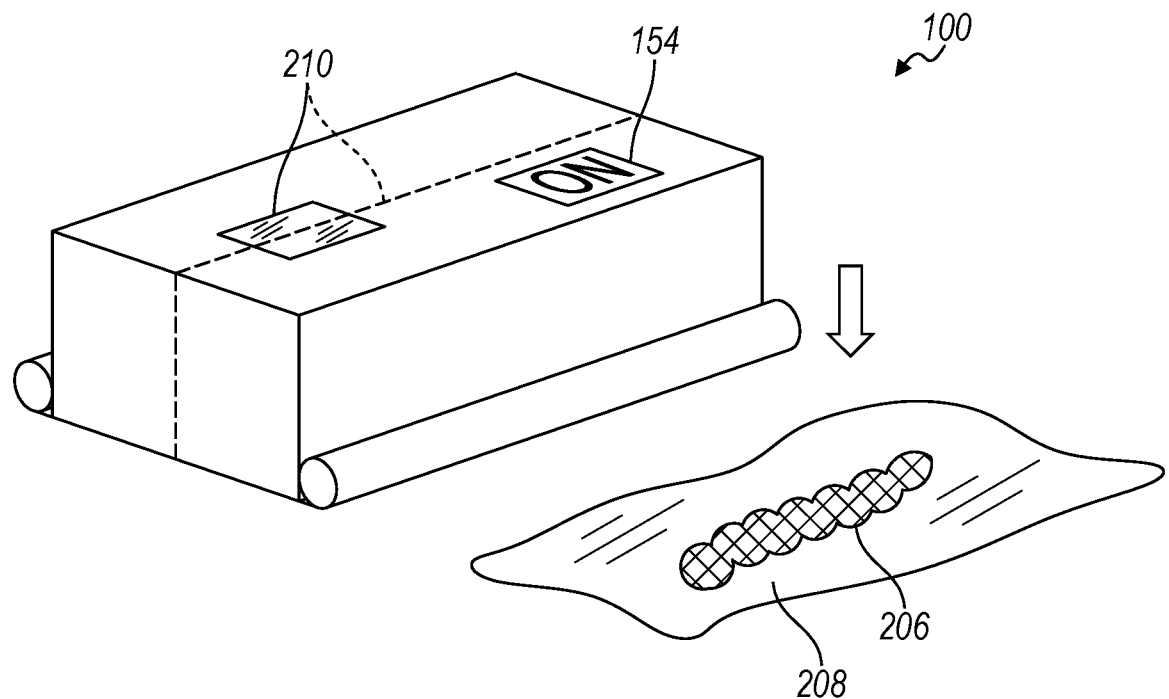
FIG. 3 illustrates a perspective view of the device of FIG. 1 according to an embodiment and in a first position.
Figure 4:
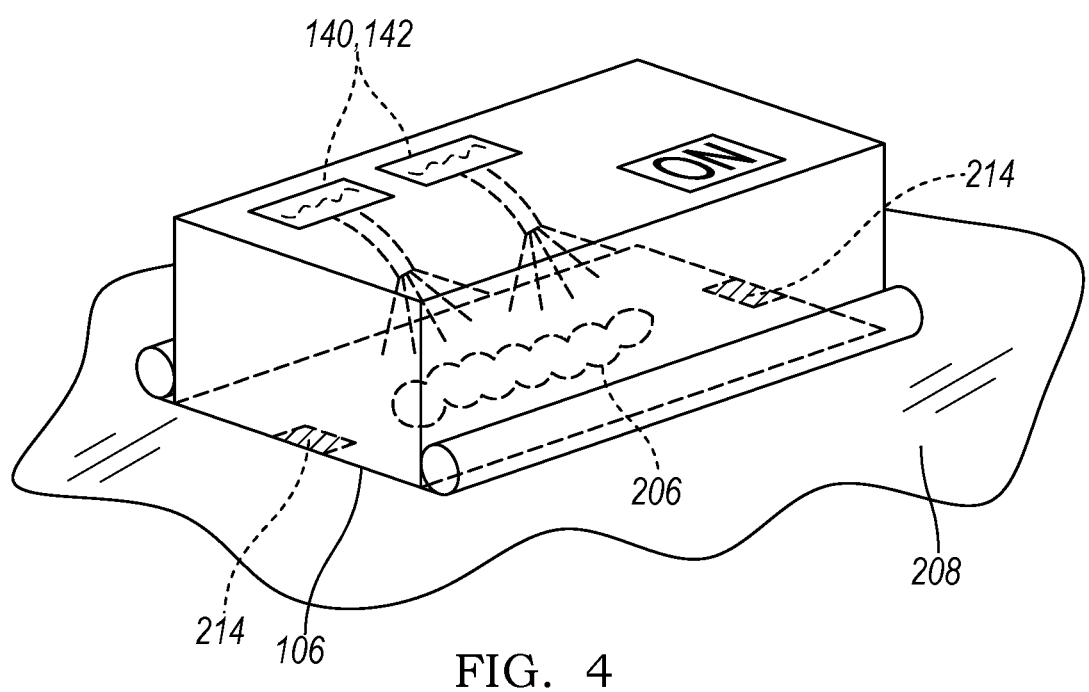
FIG. 4 illustrates a perspective view of the device of FIG. 1 according to an embodiment and in a second position.

At step 204, the device 100 is positioned over the wound 206 in the skin or tissue 208. During step 202, the device 100 is oriented with respect to the wound 206 by the user with the aid of any markings or indicators 210, including lines, transparent windows, sensors and the like. In this case, the controller 150 may send a signal to the human machine interface 154 to provide instructions to the user related to positioning and orienting the device 100 above the wound. The controller 150 and human machine interface 154 may request and require an input from the user, for example by pressing a button on the human machine interface 154, to confirm that an action has been completed before the controller 150 can proceed to the next step. FIG. 3 illustrates the device 100 above an open wound 206.

At step 212, the controller 150 initiates operation of the fluid delivery system 140 to irrigate, and/or provide a numbing, coagulant, and/or anti-septic agent to the wound 206. The lip region 106 of the housing 102 may be provided, at least in sections, with an adhesive material 214 to retain the housing 102 in its position on the tissue. Such adhesive is illustrated generally in FIG. 4 in regions 214 at opposite ends of the housing so as not to interfere with the later approximation of the wound 206. The controller 150 may activate the pressurized canister in one or more reservoirs 142, and may activate multiple reservoirs 142 in a sequential manner. Alternatively, the controller 150 may control the position of the plungers in the one or more reservoirs 142 to deliver the fluid to the wound, for example by controlling the actuator of the linear drive mechanism 112 to move an initial distance associated with the fluid delivery system 140. The human machine interface 154 may indicate to the user the step that is being performed and the status of the procedure.

Figure 5:
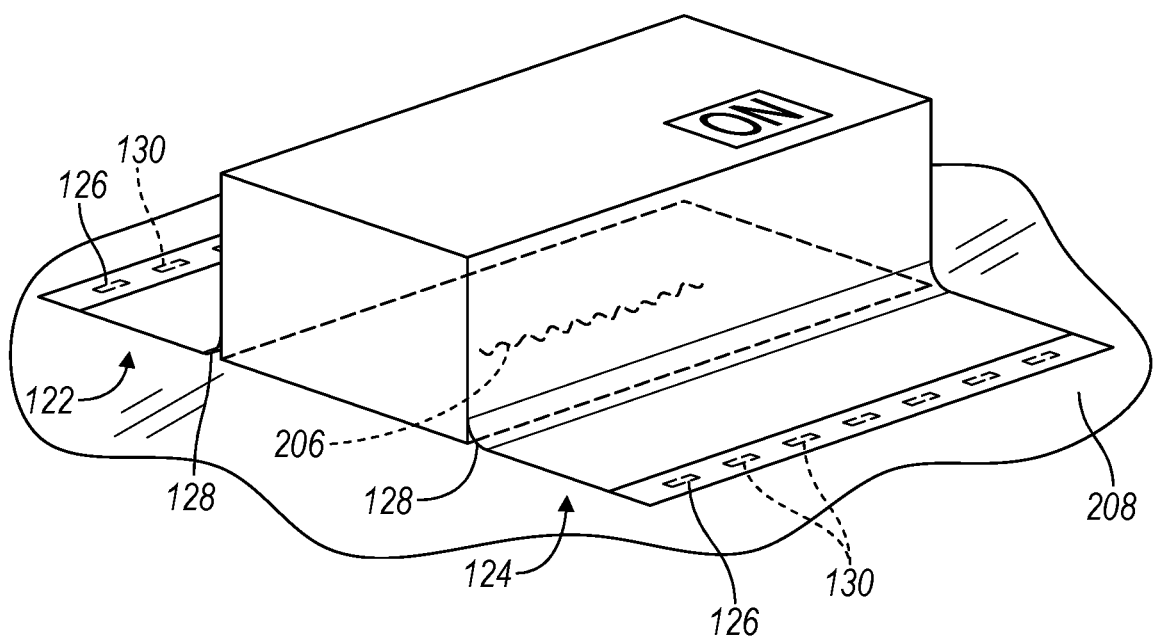
FIG. 5 illustrates a perspective view of the device of FIG. 1 according to an embodiment and in a third position.
Figure 6:
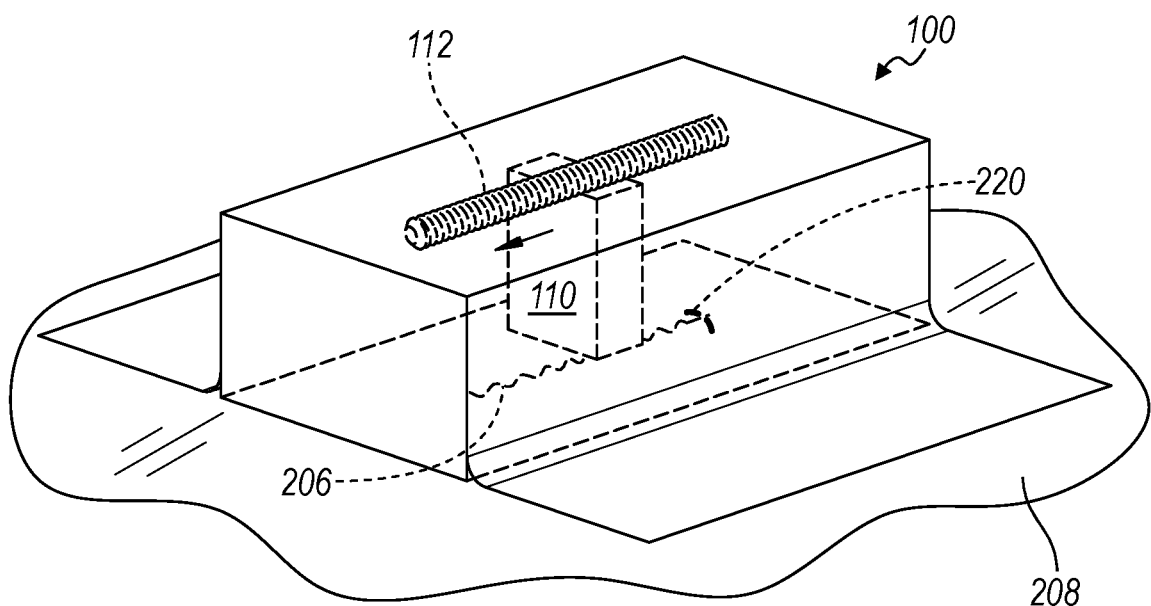
FIG. 6 illustrates a perspective view of the device of FIG. 1 according to an embodiment and in a fourth position.

At step 216, the user approximates the wound 206 using the approximation devices 122, 124, for example, in response to step-by-step instructions from the human machine interface 154. The user extends the distal end 126 of each device 122, 124 away from the housing 102, and presses the adhesive layer 130 or strip onto the underlying skin or tissue. The tensioner mechanism 128, or spring, in each device 122, 124 pulls the skin from the adhesive region 130 towards the device 100, which in turn, brings the edges of the wound 206 together and approximates the wound. The force provided by the tensioner mechanism 128 along with the distance between the distal end 126 of the device and the wound 206 may be designed to additionally provide eversion of the wound edges and improve the resulting closure. FIG. 5 illustrates the device 100 with both approximation devices 122, 124 extended and with the wound 206 approximated. The controller 150 and human machine interface 154 may provide instructions and guidance for the user to complete the actions necessary to approximate the wound using devices 122, 124, and may require confirmation from the user that the step is completed before proceeding.

At step 218, the controller 150 operates the linear drive mechanism 112 and the closure mechanism 110 to close the wound 206, for example, by suturing or stapling the tissue and edges on either side of the wound together. The closure 220 may be a running suture, a barbed suture, or a series of staples. Examples of closure mechanisms 110 are described in greater detail below. The human machine interface 154 may indicate to the user the step that is being performed and the status of the procedure.

At step 222, the human machine interface 154 indicates to the user that the procedure is completed. The human machine interface 154 may provide instructions regarding further care or treatment of the closed wound, for example, to place a protective bandage or covering over the wound, or to seek further medical attention. The human machine interface 154 may additionally provide instructions to the user for appropriate safety and disposal of the device 100, for example, to replace the cover 162 and dispose at a medical waste facility.

The human machine interface 154 and instructions provided, as well as requiring user confirmations before proceeding to the next step, may be beneficial in cases where the patient is operating the device, especially as they may be in a stage of shock, or when a person with little or no medical background is operating the device.

Figure 7:
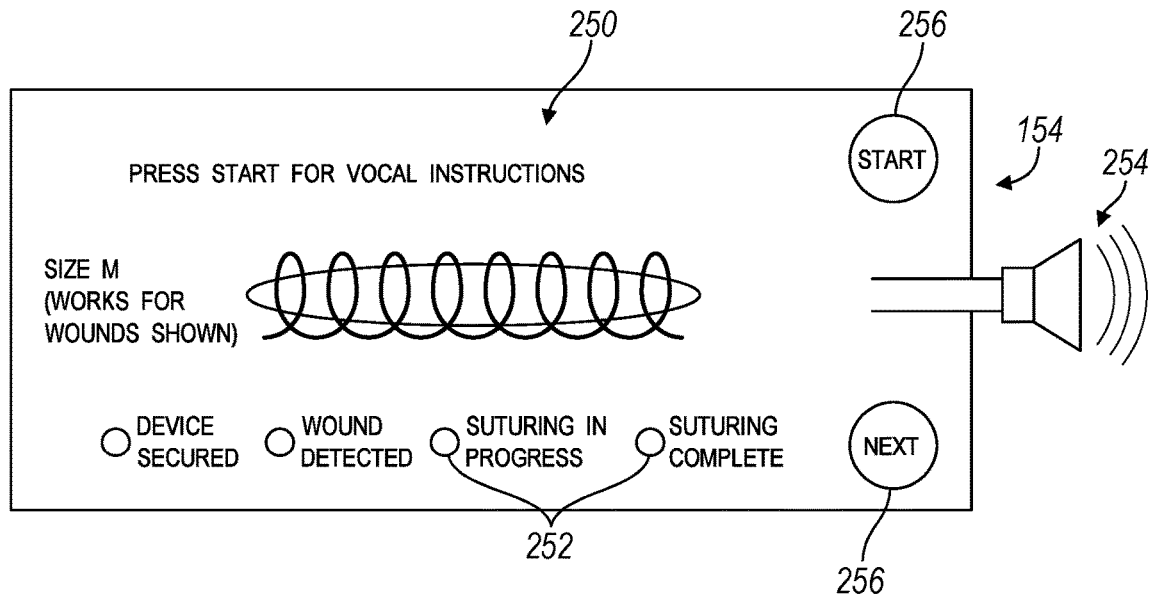
FIG. 7 illustrates a human machine interface for the device of FIG. 1 according to an embodiment.

FIG. 7 illustrates an example of a human machine interface 154 according to an embodiment. The human machine interface 154 has a display screen 250, a series of indicator lights 252, and a speaker 254. The human machine interface additionally has user inputs 256 such as an "on" button or input, and a "next" button.

Figure 8:
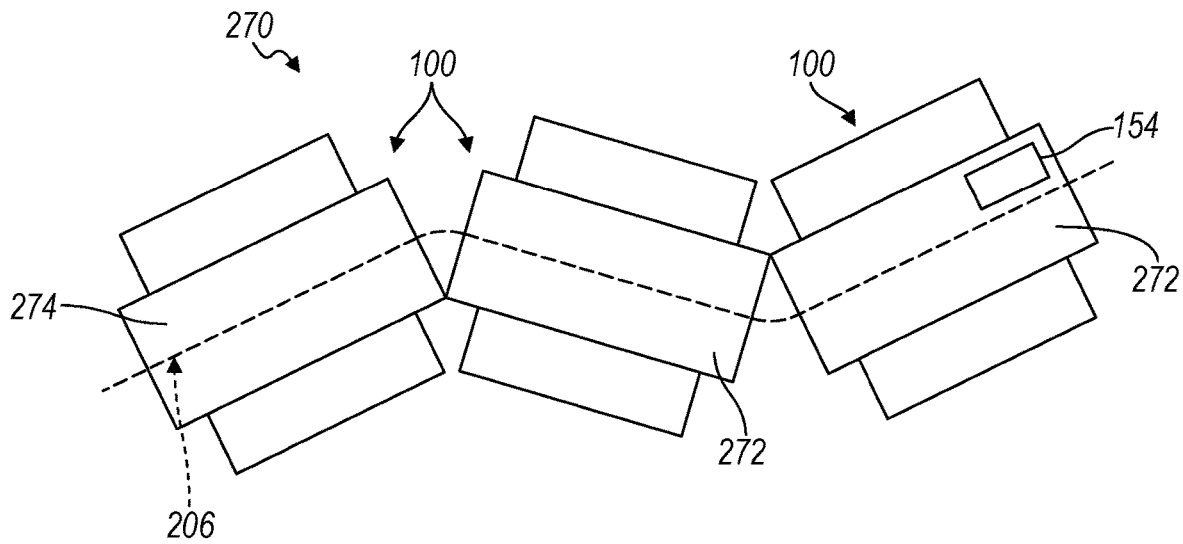
FIG. 8 illustrates a top perspective view of a system of devices according to FIG. 1.

FIG. 8 illustrates a system 270 having a series of devices 100 positioned over a wound 206 that is longer than can be closed by a single device, with the wound 206 having a non-linear shape. Although three devices 100 are illustrated for the system 270 shown in FIG. 8, any number of devices 100 may form a system 270 including two devices or four or more devices. The suture devices 100 may be linked to one another, for example, via wireless communication using the transmitters and receivers 156, 158 of each device 100. For example, the user may activate the devices 100, and the devices 100 may be configured to automatically link to one another when more than one device 100 is activated. When the devices 100 are linked, one device may act as the master device 272, with the remaining devices 274 slaved to the master device. The human machine interface 154 master device 272 may provide instructions to the user regarding various steps that the user needs to conduct for each of the devices, and request confirmation from the user that steps have been completed for all devices. The master device 272 controls the operation of all of the devices 100, and may operate them simultaneously and/or sequentially based on the step. For example, the master device 272 may operate the closure mechanisms 110 of the devices sequentially beginning with the device located on one of the ends of the wound 206. The devices 100 may additionally be equipped with positional sensors such that the master device 272 is able to determine the sequence of the devices 100 along the wound 206, and the correct order of operation for the devices 100. In other examples, the devices 100 in the system 270 may not link or communicate with one another such that the user must activate and operate each device 100 individually.

Figure 9:
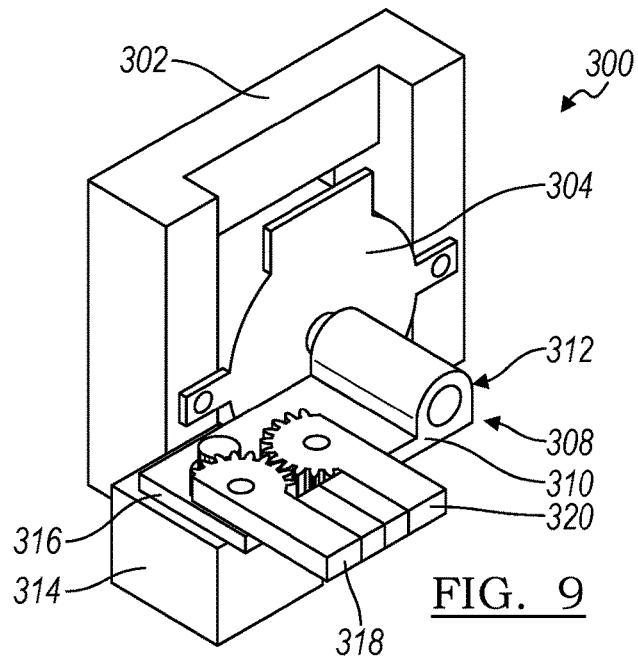
FIG. 9 illustrates a perspective view of a closure mechanism for use with the device of FIG. 1 according to an embodiment.
Figure 10:
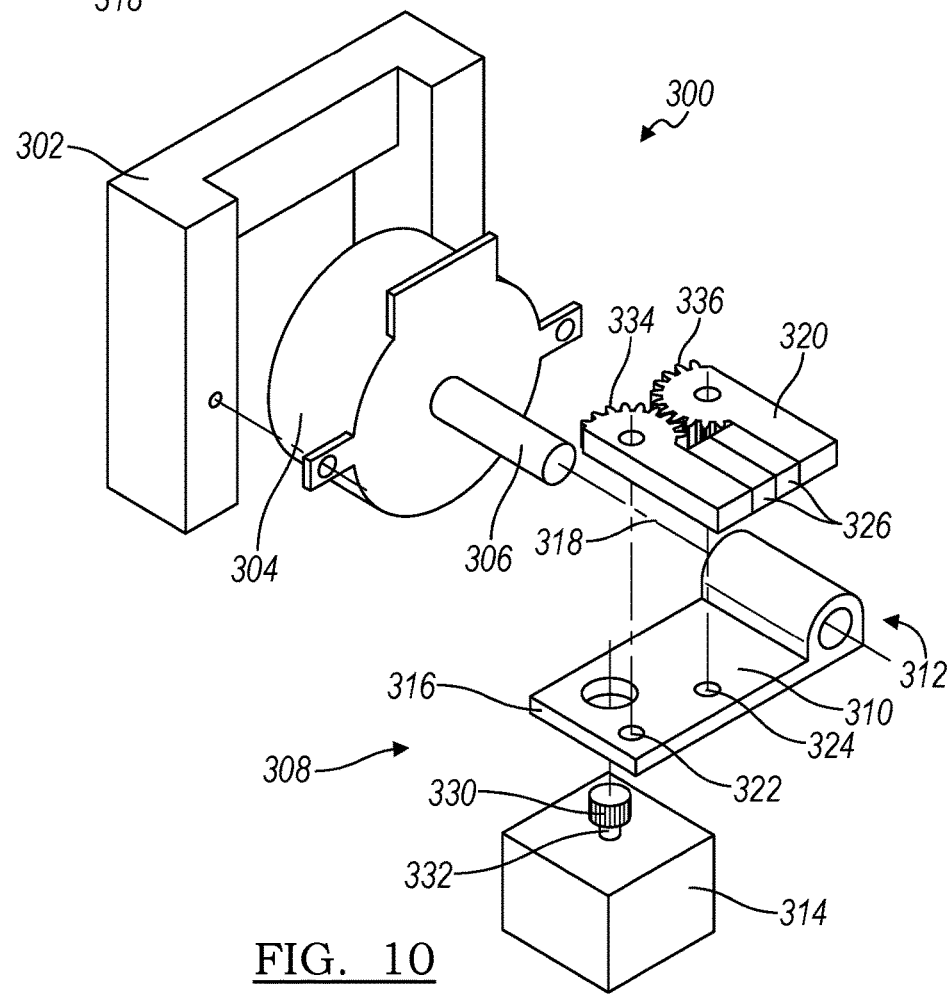
FIG. 10 illustrates an exploded view of the closure mechanism of FIG. 9.

FIGS. 9-10 illustrate a closure mechanism 300 or assembly according to an embodiment and for use as the closure mechanism 110 in the device of FIG. 1, and FIGS. 11A-G illustrate the mechanism 30 in various positions during operation.

The mechanism 300 has a bracket 302 that is configured to translate along the linear drive mechanism 112. The bracket 302 supports a motor 304. The motor 304 may be an electric motor, such as a stepper motor, and be electrically connected to the battery 152. The motor shaft 306 is connected to a claw bracket 310 of a claw assembly 308, such that the claw bracket 310 and claw assembly 308 rotates with the motor shaft 306. In one example, a first end 312 of the claw bracket 310 defines a splined surface that mates with a corresponding splined surface on the motor shaft 306. In a further example, the motor shaft 306 may additionally be provided with a gear or a series of gears that cooperate with a worm gear or threaded rod to linearly advance the bracket 302 along the linear drive mechanism 112.

The claw assembly 308 has a second motor 314 supported by second end 316 the claw bracket 310. First and second claw members 318, 320 are rotatably or pivotally connected to the claw bracket 310 at pivot points 322, 324. Each of the first and second claw members 318, 320 are provided with a gripping surface 326. The gripping surface 326 of each claw member may be textured or provided with a coating, such as a silicone or synthetic rubber, to provide improved grip on a suture needle.

A gear element 330 is provided on the shaft 332 of the second motor 314, and is meshed with a gear surface or gear head 334 on one of the claw members 318. The gear surfaces or gear heads 334, 336 of each of the claw members 318, 320 are in meshed engagement with one another. When the first claw member 318 rotates, the second claw member 320 is rotated in the opposite direction. The second motor 314 is controlled such that the motor shaft 332 rotates in a first direction to open the claw members 318, 320, and rotates in a second direction to close the claw members 318, 320 such that the gripper surfaces 326 are adjacent to one another or in contact with one another. The claw members 318, 320 and the closure mechanism 300 is configured to grasp and drive the needle and perform the suturing.

Figure 11A:
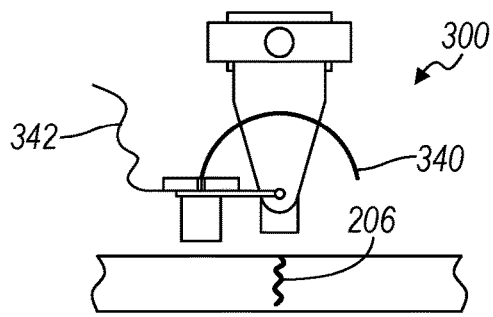
FIGS. 11A-11G illustrate schematic views of the closure mechanism of FIG. 9 in various operating stages.
Figure 11B:
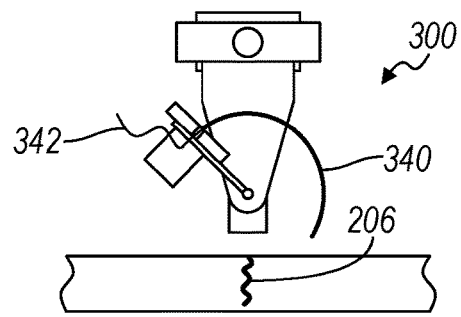
Figure 11C:
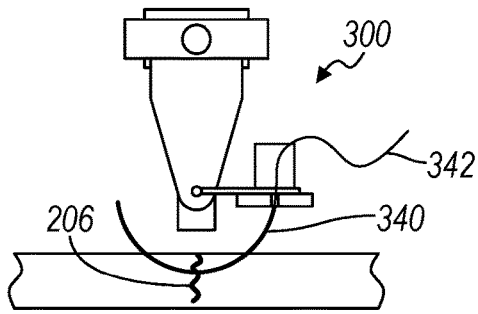
Figure 11D:
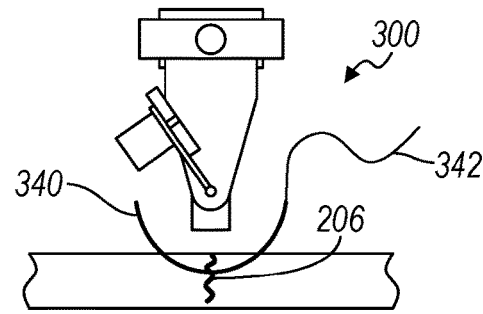
Figure 11E:
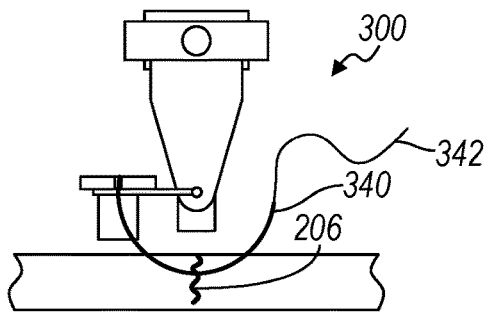
Figure 11F:
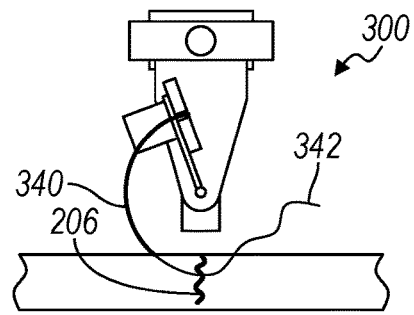
Figure 11G:
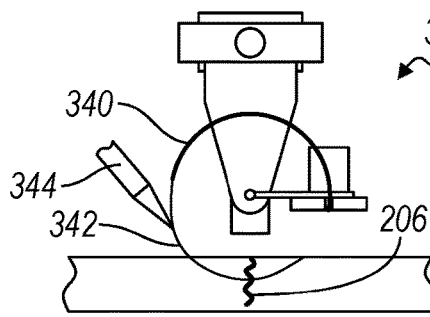

The closure mechanism 300 is pre-loaded with a needle 340 and suture 342, with the needle positioned between the claw members 318, 320. The suture may be provided as a barbed suture such that no knots are required during the procedure or at the end of the suture. As shown in FIGS. 11A-G, the second motor 314 is used to selectively open and close the claw members 318, 320 for each suturing step. The claw members 318, 320 grip the needle 340 while the claw assembly 308 is rotated until the needle 340 is inserted into the tissue and the assembly 308 is at a desired position, as shown in FIGS. 11A-B. The claw members 318, 320 are then moved by the second motor 314 to release the needle 340, and the claw assembly 308 is rotated to the opposite side of the wound by the first motor 304 in preparation for re-gripping the needle 340 as shown in FIGS. 11C-D. The claw members 318, 320 are then closed using motor 314 to re-grip the needle 340 and pull the needle and suture through the tissue, as shown in FIGS. 11E-F. These steps may be repeated for the predetermined number of sutures that the device is set to provide. In one example, the closure mechanism 300 is configured to provide three sutures via three complete rotations of the mechanism, with a linear advancement of approximately three centimeters. The mechanism 300 therefore provides three sutures spaced approximately one centimeter apart. In other examples, other numbers of sutures may be inserted for wound closure including less than three or more than three, and the mechanism 300 may conduct suturing along another linear advancement distance. The number of barbed sutures that is applied may be limited as force required to insert sutures increases with the number of sutures, as the barbed suture continues to run through the previously sutured tissue. The process ends as shown in FIG. 11G. A cutting element, such as a knife blade 344, may be provided at the second end of the translation mechanism 112 and positioned to automatically cut the needle 340 away from the suture 342 at the end of the closure procedure, and allow for the device 100 to be moved away from the skin or tissue. Additionally, the closure mechanism 110 may be advanced such that the needle is within a guard member 120 that provides sharps protection. Suturing may be advantageous over stapling, as there is more hemostasis allowed between the tissue that is brought together by the suture.

According to one example, the gripper surfaces 326 are positioned and a needle 340 curvature is selected such that the closure mechanism 300 provides a symmetrical suture. A symmetrical suture promotes wound healing, and correct alignment of the tissue layers results in reduced scar tissue formation. To create a symmetrical suture, the mechanism 300 needs to pierce the skin at a specified location and at a specified angle. The depth of the suture is targeted to be five millimeters from the skin or tissue outer surface. The needle is targeted to pierce the skin at an angle of 90°±10°. The force produced by the needle is target within a range of 1.1 Newtons to 3.5 Newtons. The approximation devices 122, 124 assist in the suture closure and accuracy by providing a targeted eversion of the wound with the edges pointed up and less than a one-millimeter gap or distance between opposed skin edges. In one example, the suture 342 is absorbable and expected to lose its tensile strength within a time period such as fourteen days, and in other examples, the suture 342 may be a permanent suture that requires removal at a later date.

The needle 340 for use in the mechanism 300 is selected based on the following factors: needle type or cross-sectional geometry, shape, radius, and curvature. In various examples, the suture needle 340 may be a tapered needle, a half circle reverse cutting needle, or other needles as are known in the art. In one example, the needle used is a circular needle with a radius of 7.64 mm, a curvature of ⅜ of a circle, and a reverse cutting needle geometry, or triangular cross-section. The curvature of the needle may increase in order to provide sufficient needle length for the claw members to grip the needle when piercing the tissue or removing from the tissue.

The motors 304, 314 may provide feedback to the controller 150 to indicate a needle force above a threshold value. This may indicate that bone or other tissue is interfering with the needle 340 path, and the controller 150 may provide a warning to the user and/or stop driving the needle and reverse the motion to remove the needle from the tissue.

Figure 12:
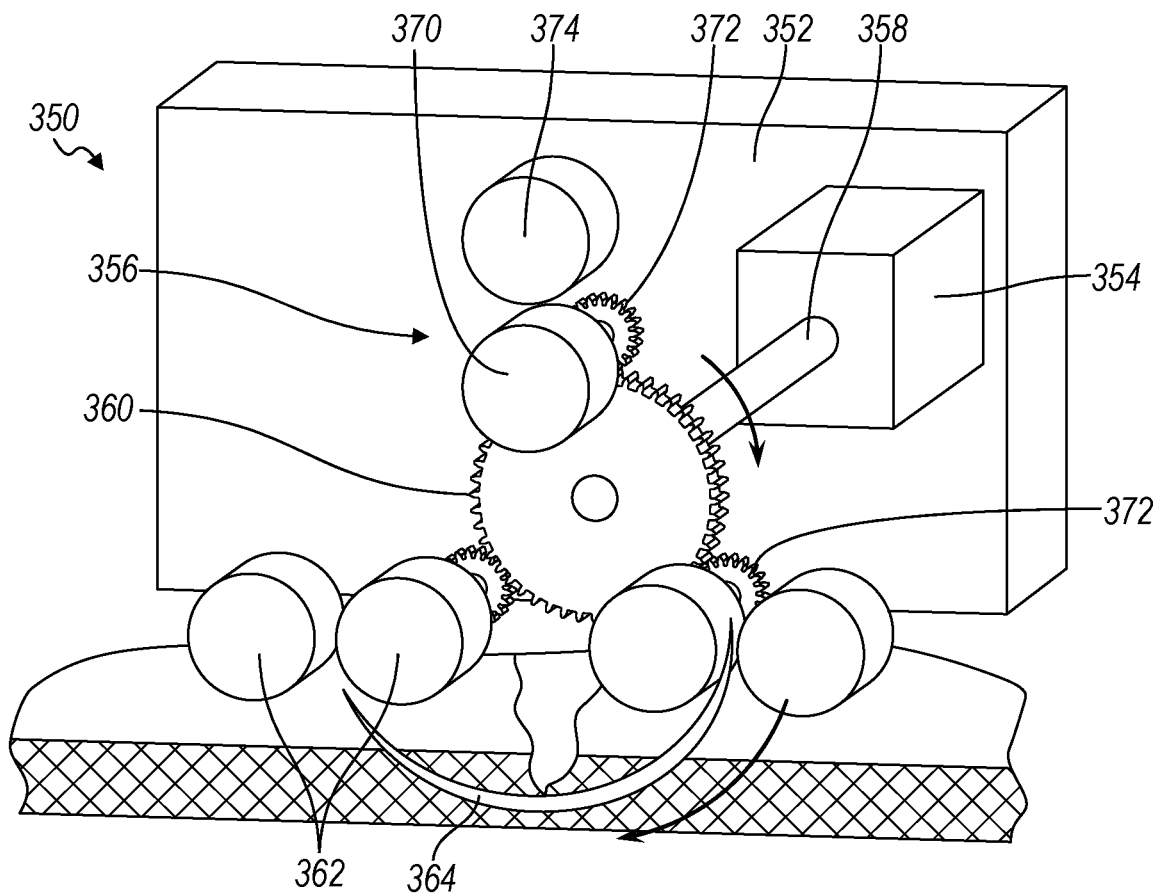
FIG. 12 illustrates a schematic view of a closure mechanism for use with the device of FIG. 1 according to another embodiment.

FIG. 12 illustrates a closure mechanism 350 according to another embodiment and for use as the closure mechanism 110 in the device of FIG. 1. In FIG. 12, the closure mechanism 350 is provided with a bracket 352 that is configured to translate along the linear drive mechanism 112. The bracket 352 supports a motor 354. The motor 354 may be an electric motor, such as a stepper motor, and be electrically connected to the battery. The motor 354 may be connected to a gear drive system 356, such as a planetary gear set. The motor shaft 358 is connected to a gear member 360, such that the gear member rotates with the motor shaft as a sun gear. In a further example, the motor shaft 358 may additionally be provided with a gear or a series of gears that cooperate with a worm gear or threaded rod to linearly advance the bracket 352.

A series of pairs of rollers 362 are arranged circumferentially about the gear element 360, and in one example, the closure mechanism has three pairs of rollers 362, although another number of pairs of rollers is also contemplated. The outer surfaces of each roller may be textured or provided with a coating, such as a silicone or synthetic rubber, to provide improved grip on a suture needle. The rollers in each pair of rollers 362 may be in contact with one another or have a predetermined spacing between one another to provide a desired force on a suture needle 364 positioned therebetween.

The positioning and geometry of the pairs of rollers 362 is based on the suture needle geometry. The closure mechanism 350 is pre-loaded with a needle 364 and suture 366, with the needle positioned between at least one pair of the rollers. The positioning of the pairs of rollers 362 is coordinated with the curvature of the suture needle such that a radius of curvature of a circle defined by the interfaces between each of the rollers is similar to or the same as the curvature of the suture needle. The size and diameter of the rollers may be the same or may be different from one another. The diameter of the rollers may be selected based on the radius of curvature of the suture needle, the desired contact area with the suture needle, and to provide for entry of the suture needle into a pair of rollers while allowing for a degree of variability in the position of the needle tip relative to the prescribed needle path.

Similarly to that described above with respect to FIGS. 9-10, the suture may be provided as a barbed suture such that no knots are required during the procedure or at the end of the suture. The closure mechanism as shown in FIG. 12 may provide a symmetrical suture with the characteristics as described above with respect to FIGS. 9-10. A cutting element, such as a knife blade, may be provided at the second end of the translation mechanism and positioned to automatically cut the needle away from the suture at the end of the closure procedure, and allow for the device to be moved away from the skin or tissue. Additionally, the closure mechanism 350 may be advanced such that the needle is within a guard member 120 that provides sharps protection. The suture may be guided or otherwise led into the closure mechanism 350 to prevent entanglement with the rollers and gears.

For each pair of rollers 362, a first roller 370 of the pair of rollers may be connected to a gear member 372, such as a planetary gear, that is in meshed engagement with and rotated by the sun gear 360. The second roller 374 in each pair of rollers may be rotatably connected to a mounting bracket 352 or another fixed structure acting as the ring gear member, such that it freely rotates. Alternatively, the second roller 374 may be connected to a gear member in meshed engagement or otherwise driven by the gear member 372 of the first roller 370, such that both the first and second rollers 370, 374 are rotatably driven by the sun gear 360.

The gear member 360 is driven in rotation by the motor shaft 358, and drives the gear 372 connected to each of the first rollers 370 thereby rotating the first rollers 370 in a first direction. In some examples, a gear connected to each of the second rollers 374 is driven by the first gear 372 to rotate the second rollers 374 in a second direction, with the second direction being opposite to the first direction to feed and drive the needle 364 through the rollers. The first and second rollers 370, 374 may be driven at the same rotational speed. In other examples, only the first roller 370 is driven by the gear member 360, and the second roller 374 freely rotates. The first and second rollers 370, 374 cooperate to advance a suture needle 364 when one is positioned therebetween.

In one example, the closure mechanism 350 is configured to provide three sutures via three complete rotations of the mechanism, with a linear advancement of approximately three centimeters. The mechanism 350 therefore provides three sutures spaced approximately one centimeter apart by controlling the motor 354 to provide three complete revolutions of the suture needle. In other examples, other numbers of sutures may be inserted for wound closure including less than three or more than three, and the mechanism may conduct suturing along another linear advancement distance.

Figure 13:
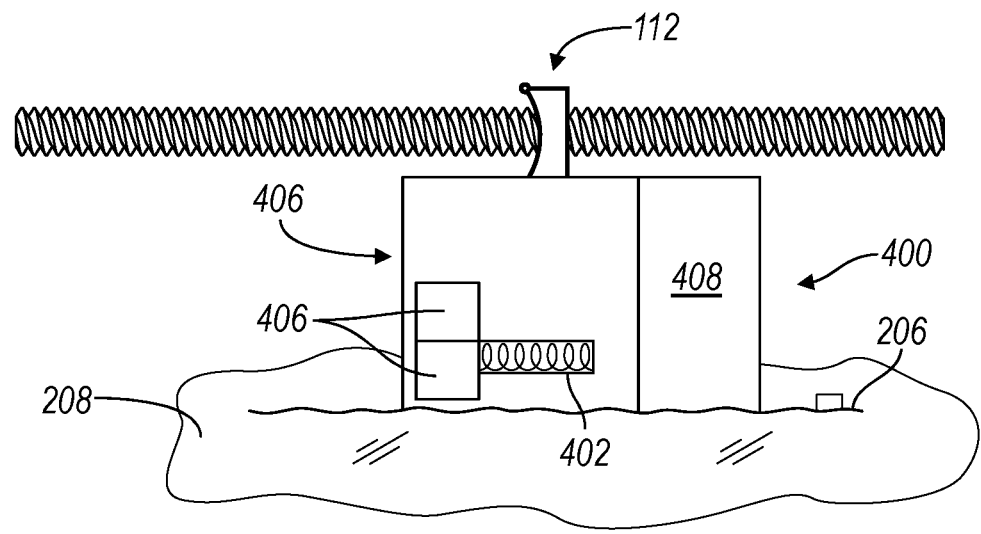
FIG. 13 illustrates a schematic view of a closure mechanism for use with the device of FIG. 1 according to yet another embodiment.

FIG. 13 illustrates a closure mechanism 400 according to yet another embodiment and for use with the device of FIG. 1. The closure mechanism 400 provides a series of fasteners such as staples or clips to close the wound or laceration. The closure mechanism includes a cartridge 402 of fasteners provided within the interior of the housing, and a fastener device 404 such as a stapler. The translational drive mechanism 112 may drive the cartridge of fasteners in conjunction with the fastener device as shown, or the cartridge may be fixed within the housing such that only the fastener device is moved by the translational drive mechanism. In one example, the closure mechanism 400 is sized to provide three fasteners, such as staples, along a three-centimeter length wound or laceration, with approximately one-centimeter separation between each fastener.

The fastener device 404 may be provided according to various surgical staplers or automatic clip applicators as are known in the art. In one example, the fastener device 404 is provided with various components 406 to advance a fastener, trigger the implantation of a fastener, position and align the fastener relative to the skin, and form the fastener from a pre-implantation shape to a post-implantation shape. The fastener device 404 may be electrically powered and include an electric motor 408. The fastener device 404 may additionally incorporate various spring members, forming surfaces, and the like to control operation and insertion of the staples or fasteners.

According to one aspect, a portable, single use device is provided with a housing, first and second approximation members supported by the housing, a wound closure mechanism supported for translation within the housing by a translational drive mechanism, and a controller configured to operate the wound closure mechanism and translational drive mechanism. In further aspects, the devices may be provided with a fluid delivery system operably controlled by the controller, or a human machine interface in communication with the controller and configured to provide instructions and/or alerts to the user. In a further aspect, the wound closure mechanism is provided by one of a suturing mechanism and a stapling mechanism. A system of devices may be provided and are configured to communicate with one another to close a wound with a length greater than a single device is configured to close.

According to another aspect, an automatic suturing mechanism is provided with a first electric motor supported by a bracket, a claw bracket connected to a shaft of the first electric motor for rotation therewith, a second electric motor connected to the claw bracket, and first and second claw members rotatably connected to the claw bracket. Each claw member has a gripping surface. The first claw member driven by the second electric motor and configured to move between a first position with the gripping surfaces of the first and second claw members in contact with one another and a second position with the gripping surfaces of the first and second claw members spaced apart from one another.

According to yet another aspect, another automatic suturing mechanism is provided with a support frame, an electric motor, and pairs of rollers supported by the support frame and spaced apart from one another about the frame such that a suture needle may be passed from one pair of rollers to a subsequent adjacent pair of rollers along a path forming a continuous loop. A gear mechanism drivingly connects the driveshaft of the motor with at least one of the rollers in each pair of rollers. In a further aspect, the gear mechanism is provided by a planetary gearset.

According to another aspect, a method of closing a wound is provided. A wound closure device is positioned over a wound. Approximation members extended away from the device housing and pull the skin or tissue on either side of the wound towards the wound. A controller controls a wound closure mechanism and a translational drive mechanism of the device to close a wound. In further aspects, the steps are performed sequentially, the controller operates a fluidly delivery system to irrigate and/or sterilize the wound prior to approximation, the controller operates the device in response to a request from a user via a human machine interface, or the controller communicates with the human machine interface to provide instructions and/or alerts to a user.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A medical wound closure device for portable and single usage, the device comprising:
   a housing;
   first and second approximation members supported by the housing, each approximation member having a distal end region configured to move from a first position adjacent to the housing to a second position spaced apart from the housing to approximate a wound;
   a wound closure mechanism supported for translation on a support frame within the housing by a translational drive mechanism, the wound closure mechanism configured to insert at least one suture into tissue to close the wound, the wound closure mechanism further comprising:
   an electric motor connected to the support frame and having a driveshaft,
   a series of pairs of rollers supported by the support frame for rotation relative to the support frame; each pair of rollers spaced apart from adjacent pairs of rollers about the frame such that a suture needle may be passed from one pair of rollers to a subsequent adjacent pair of rollers along a path forming a continuous loop, and
   a gear mechanism drivingly connecting the driveshaft of the motor with at least one of the rollers in each pair of rollers, wherein the gear mechanism comprises a planetary gearset having a sun gear connected for rotation with the driveshaft of the motor, and a series of planetary gears in meshed engagement with the sun gear, each planetary gear connected for rotation with the at least one of the rollers in each pair of rollers; and
   a controller configured to operate the translational drive mechanism to move the wound closure mechanism relative to the housing, and operate the wound closure mechanism to insert the at least one suture.

2. The device of claim 1 further comprising a human machine interface in communication with the controller and configured to provide instructions to a user.

3. The device of claim 1 further comprising a cutting element supported by the housing and positioned to cut the at least one suture.

4. The device of claim 1 further comprising at least one visual positioning indicator supported by the housing and configured for use in aligning the housing relative to the wound by a user, the at least one visual positioning indicator being at least one of a visual marking and a transparent region of the housing.

5. The device of claim 1 further comprising a fluid delivery system supported by the housing and operably controlled by the controller.

6. The device of claim 5 wherein the fluid delivery system has a reservoir containing an irrigation and/or sterilization fluid.

7. A system comprising:
a plurality of devices according to claim 1 positioned adjacent to one another along the wound, the plurality of devices configured to communicate with one another to close the wound with a length greater than a single device is configured to close.

8. An automatic suturing mechanism comprising: a support frame; an electric motor connected to the support frame and having a driveshaft; a series of pairs of rollers supported by the support frame for rotation relative to the support frame; each pair of rollers spaced apart from adjacent pairs of rollers about the frame such that a suture needle may be passed from one pair of rollers to a subsequent adjacent pair of rollers along a path forming a continuous loop; and
a gear mechanism drivingly connecting the driveshaft of the motor with at least one of the rollers in each pair of rollers, wherein the gear mechanism comprises a planetary gearset having a sun gear connected for rotation with the driveshaft of the motor, and a series of planetary gears in meshed engagement with the sun gear, each planetary gear connected for rotation with the at least one of the rollers in each pair of rollers.

9. The automatic suturing mechanism of claim 8 wherein the series of pair of rollers comprises three pairs of rollers, one pair of rollers spaced equidistant from the other pairs of rollers.

10. The automatic suturing mechanism of claim 8 wherein the other one of the rollers in each pair of rollers is rotatably connected to a mounting bracket acting as a ring gear member, such that it freely rotates relative to the at least one of the rollers in each pair of rollers.

* * * * *